United States Patent
Kirkwood et al.

(10) Patent No.: US 10,901,115 B2
(45) Date of Patent: Jan. 26, 2021

(54) LOGGING OF FLUID PROPERTIES FOR USE IN SUBTERRANEAN DRILLING AND COMPLETIONS

(71) Applicant: Halliburton Energy Services, Inc., Houston, TX (US)

(72) Inventors: Andrew Douglas Kirkwood, Houston, TX (US); Christopher Michael Jones, Katy, TX (US); Darren Gascooke, Houston, TX (US); Michael T. Pelletier, Houston, TX (US); Anthony Herman van Zuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 78 days.

(21) Appl. No.: 16/324,314

(22) PCT Filed: Sep. 29, 2016

(86) PCT No.: PCT/US2016/054491
§ 371 (c)(1),
(2) Date: Feb. 8, 2019

(87) PCT Pub. No.: WO2018/063254
PCT Pub. Date: Apr. 5, 2018

(65) Prior Publication Data
US 2020/0041689 A1 Feb. 6, 2020

(51) Int. Cl.
*E21B 49/08* (2006.01)
*G01V 9/00* (2006.01)
(Continued)

(52) U.S. Cl.
CPC .......... *G01V 9/00* (2013.01); *E21B 7/04* (2013.01); *E21B 44/02* (2013.01); *E21B 49/087* (2013.01);
(Continued)

(58) Field of Classification Search
CPC ........ G01N 33/2823; G01V 9/00; E21B 7/04; E21B 44/02; E21B 49/087; E21B 49/0875; E21B 43/16
See application file for complete search history.

(56) References Cited

U.S. PATENT DOCUMENTS

| | | |
|---|---|---|
| 2004/0140091 A1 | 7/2004 | Gupta |
| 2009/0288881 A1 | 11/2009 | Mullins et al. |

(Continued)

FOREIGN PATENT DOCUMENTS

WO 2014/113528 A1 7/2014

OTHER PUBLICATIONS

International Search Report and Written Opinion issued in related PCT Application No. PCT/US2016/054491 dated Jun. 7, 2017, 16 pages.

(Continued)

*Primary Examiner* — Yong-Suk (Philip) Ro
(74) *Attorney, Agent, or Firm* — John W. Wustenberg; Baker Botts L.L.P.

(57) ABSTRACT

Systems and methods for placing well bores and/or portions of completed well systems in a subterranean formation relative to tar mats or other phenomena in the formation are provided. In some embodiments, the methods comprise: identifying a reservoir characteristic associated with a (Continued)

chemical or physicochemical property of a fluid in or proximate to the reservoir characteristic; measuring the property of a fluid in at least a portion of a subterranean formation in two or more locations in the subterranean formation; identifying a variation of the property of the fluid at one or more of the locations in the subterranean formation; and determining a target location or direction for a portion of a well system based at least in part on the variation of the property of the fluid, the well system comprising a borehole penetrating the subterranean formation.

20 Claims, 6 Drawing Sheets (51) Int. Cl.
    *E21B 7/04*     (2006.01)
    *E21B 44/02*     (2006.01)
    *G01N 33/28*     (2006.01)
    *E21B 43/16*     (2006.01)

(52) U.S. Cl.
    CPC .......... *G01N 33/2823* (2013.01); *E21B 43/16* (2013.01); *E21B 49/0875* (2020.05)

(56) References Cited

U.S. PATENT DOCUMENTS

| | | | |
|---|---|---|---|
| 2011/0228637 A1 | 9/2011 | Zamow et al. | |
| 2011/0246143 A1* | 10/2011 | Pomerantz | E21B 49/00 703/2 |
| 2014/0260586 A1* | 9/2014 | Van Hal | E21B 49/082 73/152.07 |
| 2017/0204711 A1* | 7/2017 | Howell | E21B 47/07 |

OTHER PUBLICATIONS

Buchanan, Andrew, et al. "Geomagnetic Referencing—The Real-Time Compass for Directional Drillers." Oilfield Review 25.3 (2013): 32-47.
Bourgeois, Tim J., et al. "Pushing the Limits of Formation Evaluation While Drilling." Oilfield Review 9.4 (1997): 32-47.
Bargach, Saad, et al. "Real-time LWD: logging for drilling." Oilfield Review 12.3 (2000): 58-78.
Nascimento, Joho de DS, and Ricardo MR Gomes. "Tar Mats Characterization From Nmr and Conventional Logs, Case Studies in Deepwater Reservoirs, Offshore Brazil." SPWLA 45th Annual Logging Symposium. Society of Petrophysicists and Well-Log Analysts, 2004.

* cited by examiner

LOGGING OF FLUID PROPERTIES FOR USE IN SUBTERRANEAN DRILLING AND COMPLETIONS

CROSS-REFERENCE TO RELATED APPLICATION

The present application is a U.S. National Stage Application of International Application No. PCT/US2016/054491 filed Sep. 29, 2016, which is incorporated herein by reference in its entirety for all purposes.

TECHNICAL FIELD

The present disclosure relates generally to drilling and/or completing well bores in subterranean formations, and more particularly, to methods of placing well bores and/or portions of completed well systems in a subterranean formation relative to reservoir characteristics such as tar mats in the formation.

BACKGROUND

Modern petroleum drilling and production operations demand a great quantity of information relating to the parameters and conditions downhole. Such information typically includes the location and orientation of the borehole and drilling assembly, earth formation properties, and parameters of the downhole drilling environment. The collection of information relating to formation properties and downhole conditions is commonly referred to as "logging", and can be performed during the drilling process itself (hence the term "logging while drilling" or "LWD"). Techniques known as geosteering may be used to control the direction in which a well bore is drilled based on logging measurements in the formation.

Various measurement tools exist for use in wireline logging and LWD. One such tool is the resistivity tool, which includes one or more antennas for transmitting an electromagnetic signal into the formation and one or more antennas for receiving a formation response. When operated at low frequencies, the resistivity tool may be called an "induction" tool, and at high frequencies it may be called an electromagnetic wave propagation tool. Though the physical phenomena that dominate the measurement may vary with frequency, the operating principles for the tool are consistent. In some cases, the amplitude and/or the phase of the receive signals are compared to the amplitude and/or phase of the transmit signals to measure the formation resistivity. In other cases, the amplitude and/or phase of the receive signals are compared to each other to measure the formation resistivity.

In certain situations, such as when drilling through formations in which the formation boundaries extend vertically, or when drilling from an off-shore platform, it is desirable to drill wells at an angle with respect to bed boundaries in the strata. This is often termed "horizontal" drilling. When drilling horizontally, it is desirable to maintain the well bore in the pay zone (the formation which contains hydrocarbons) as much as possible so as to maximize the recovery. This can be difficult since formations may dip or divert. In many cases, it may be desirable to drill the "horizontal" section of a well bore at a particular depth, among other reasons, in order to maintain the well bore within a zone of interest and/or to minimize breakthrough of water or other substances from other zones of the formation.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

Illustrative embodiments of the present disclosure are described in detail herein. In the interest of clarity, not all features of an actual implementation are described in this specification. It will of course be appreciated that in the development of any such actual embodiment, numerous implementation specific decisions must be made to achieve developers' specific goals, such as compliance with system related and business related constraints, which will vary from one implementation to another. Moreover, it will be appreciated that such a development effort might be complex and time consuming, but would nevertheless be a routine undertaking for those of ordinary skill in the art having the benefit of the present disclosure. Furthermore, in no way should the following examples be read to limit, or define, the scope of the disclosure.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. The information handling system may also include one or more interface units capable of transmitting one or more signals to a controller, actuator, or like device.

For the purposes of this disclosure, computer-readable media may include any instrumentality or aggregation of instrumentalities that may retain data and/or instructions for a period of time. Computer-readable media may include, for example, without limitation, storage media such as a direct access storage device (for example, a hard disk drive or floppy disk drive), a sequential access storage device (for example, a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

The terms "couple" or "couples" as used herein are intended to mean either an indirect or a direct connection. Thus, if a first device couples to a second device, that connection may be through a direct connection or through an indirect mechanical or electrical connection via other devices and connections. Similarly, the term "communicatively coupled" as used herein is intended to mean either a direct or an indirect communication connection. Such connection may be a wired or wireless connection such as, for example, Ethernet or local area network (LAN). Such wired and wireless connections are well known to those of ordinary skill in the art and will therefore not be discussed in detail herein. Thus, if a first device communicatively couples to a second device, that connection may be through a direct connection, or through an indirect communication connection via other devices and connections.

Certain embodiments according to the present disclosure may be directed to systems and methods for use in connection with drilling and/or completing well bores in subterranean formations, and more particularly, to methods of placing well bores and/or portions of completed well systems in a subterranean formation relative to tar mats or other phenomena in the formation. In particular, the methods and systems of the present disclosure measure and use properties of a fluid (e.g., drilling fluid, formation fluid, etc.) in the formation to detect certain reservoir characteristics in a formation, which may include phenomena such as tar mats, salt domes, brittle shale zones, or other types of characteristics. In the methods of the present disclosure, a property of a fluid may be identified that is associated with a particular reservoir characteristic of interest. This association of a reservoir characteristic with a fluid property may be known in the art, or may be newly-discovered in a particular application of the present disclosure. The selected property of fluids in the formation may be measured in multiple locations in the formation, for example, at multiple depths along the length of a borehole drilled to penetrate the formation. Because of the aforementioned relationship, a variation in the property of the fluid in a particular location in the formation (e.g., at a particular depth in the borehole) may indicate the location or depth of the reservoir characteristic of interest. Based on that location, a target location in the formation for a portion of a well system may be identified. This target location may be used for determining or designing various aspects of a well system, such as the bottomhole depth of a borehole, the location of a kickoff point of a borehole being drilled, the interval in a well at which certain completions equipment (e.g., casing, tubing, packers, plugs, seals, etc.) will be installed, the interval in a well at which certain treatments or completions operations (e.g., perforation, stimulation, cementing, workover, etc.) will be performed, and the like. The boreholes and/or well bores in the well systems of the present disclosure may comprise injection wells, hydrocarbon-producing wells, water-producing wells, test wells, and the like.

Among the many potential advantages to the methods and compositions of the present disclosure, only some of which are alluded to herein, the methods and systems of the present disclosure may facilitate effective placement of well bores and components of well systems in drilling and/or completions operations. In certain embodiments, the methods and systems of the present disclosure may be able to identify the location certain reservoir characteristics more reliably, accurately, earlier (e.g., at a greater distance away from them) in the drilling process, and/or with fewer false positives as compared to other methods, which may enable more effective well system design relative to various phenomena in the formation. In certain embodiments, the methods and systems of the present disclosure may rely primarily and/or exclusively on downhole measurements of fluid properties, which may reduce or alleviate the additional cost and delay associated with retrieving fluid samples from the well bore for surface analysis.

For example, certain embodiments of the present disclosure may be used to identify the location of a tar mat (e.g., a region in a subterranean formation having high asphaltene concentrations and/or fluids of high viscosity) in a subterranean formation. When drilling injection wells in subterranean formations (e.g., wells into which water, steam, gases, or other fluids are injected to sweep across a portion of a formation to deliver treatment chemicals and/or displace fluids therein), it is often desirable to drill the well to a vertical depth just above any tar mat in the formation, among other reasons, to allow for effective sweeping of the reservoir while avoiding problematic pressure build-ups that can result if fluids are injected below the tar mat. The methods and systems of the present disclosure may be used to determine the location of the tar mat in a formation based at least in part on compositional data from fluids in the formation. This compositional data may be obtained using wireline measurements taken in an existing borehole, MWD/LWD measurements obtained while drilling a new borehole (e.g., the injection well itself), or a combination thereof. In these embodiments, an injection well may be drilled to a depth corresponding to or chosen based on the location where the variation in a compositional property of a fluid is detected. Of course, as a person of skill in the art will recognize, the methods and systems of the present disclosure may be used to determine the location of various different types of reservoir characteristics in a similar manner.

Figure 1:
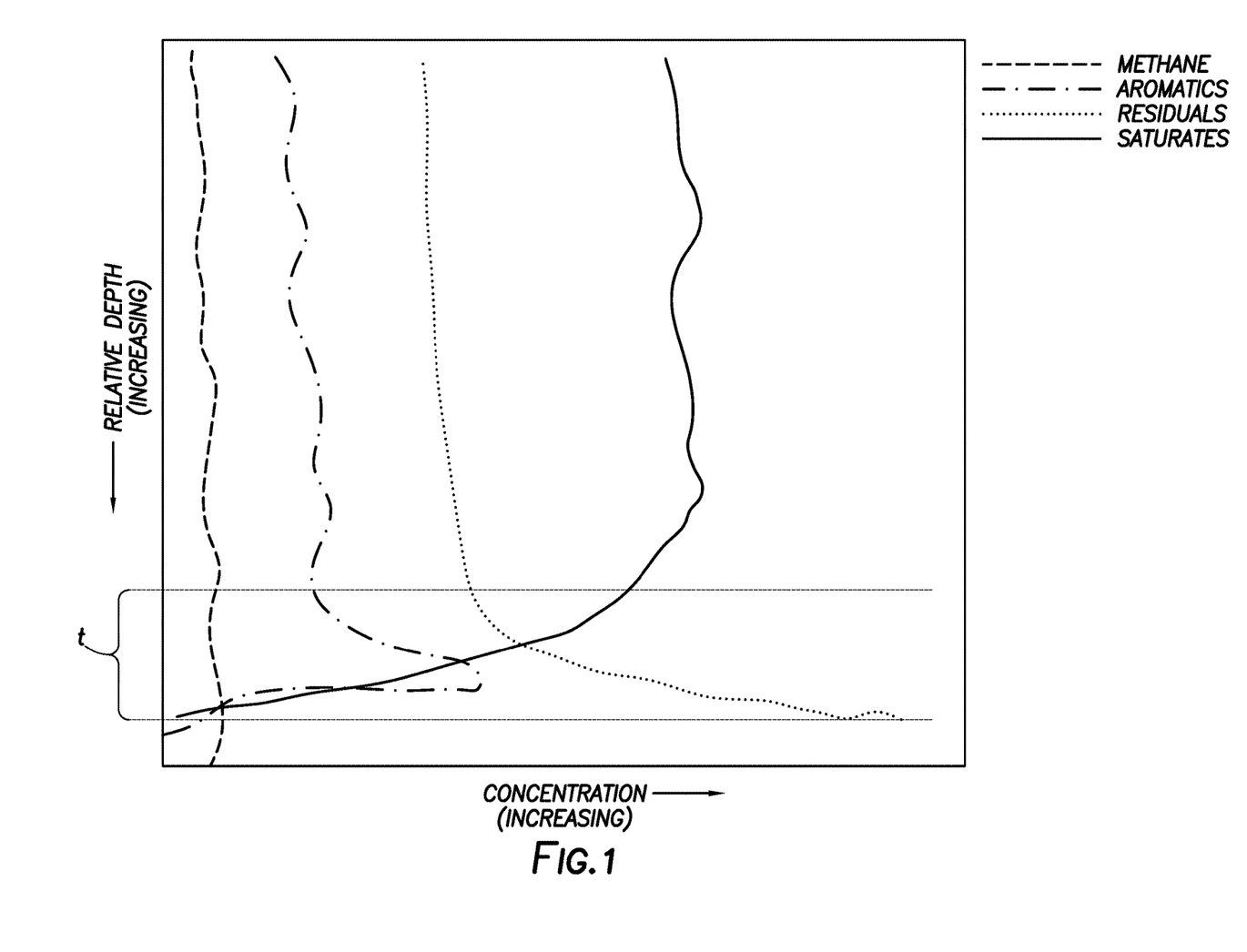
FIG. 1 is an idealized plot showing data regarding certain fluid properties in a subterranean formation in accordance with one or more aspects of the present disclosure.

One natural phenomenon that may be associated with certain subterranean tar mats is rapid transitioning of fluid composition near the tar mat. For example, referring now to FIG. 1, an idealized plot of certain properties of fluids in a subterranean formation (i.e., concentrations of methane, propene, saturates, aromatics, and residuals) as a function of relative depth in the formation is shown. As shown in FIG. 1, the concentration of aromatic species such as various hydrocarbon aromatics, asphaltenes or resins may exhibit a sharp increase in fluids in a transitional region at relative depth range t just above a tar mat, and then may decrease rapidly below the tar mat. Similarly, the concentrations of saturates may decrease in that same region at depth range t. Thus, in certain embodiments, the presence of a tar mat may be detected by monitoring compositional data from the formation for a significant variation in one or more of these properties individually and/or in the ratio of the respective concentrations aromatics to saturates. In certain embodiments, based on this information, an injection well may be drilled to a vertical depth just above the depth where the ratio of aromatics to saturates in the fluids is observed or extrapolated to be at its highest, or within some distance of that depth.

The methods and systems of the present disclosure may be used to design and/or deploy well systems relative to any reservoir characteristic found in subterranean formations, including but not limited to tar mats, salt domes, hydrocarbon-bearing regions, water-bearing regions, brittle shale zones, laterally continuous zones, lateral zones of sufficient permeability, or other types of formations. The particular characteristic may be correlated or otherwise associated with any chemical or physicochemical property of a fluid that can be measured in a subterranean formation. Physicochemical properties are physical properties that may be derived compositionally. Examples of physicochemical properties include but are not limited to pH, density, optical density, nuclear magnetic resonance (NMR) properties, viscosity, viscoelasticity, compressibility, thermal conductivity, heat capacity, mass diffusion, and the like. Compositional fluid properties that may be used in certain embodiments of the present disclosure include, but not limited to: concentrations of aromatic species (e.g., asphaltenes, resins, etc.), saturated species, and the like; concentrations of specific chemical compounds (e.g., methane); ratios of the concentrations of different chemical types or compounds; and the like.

Figure 4:
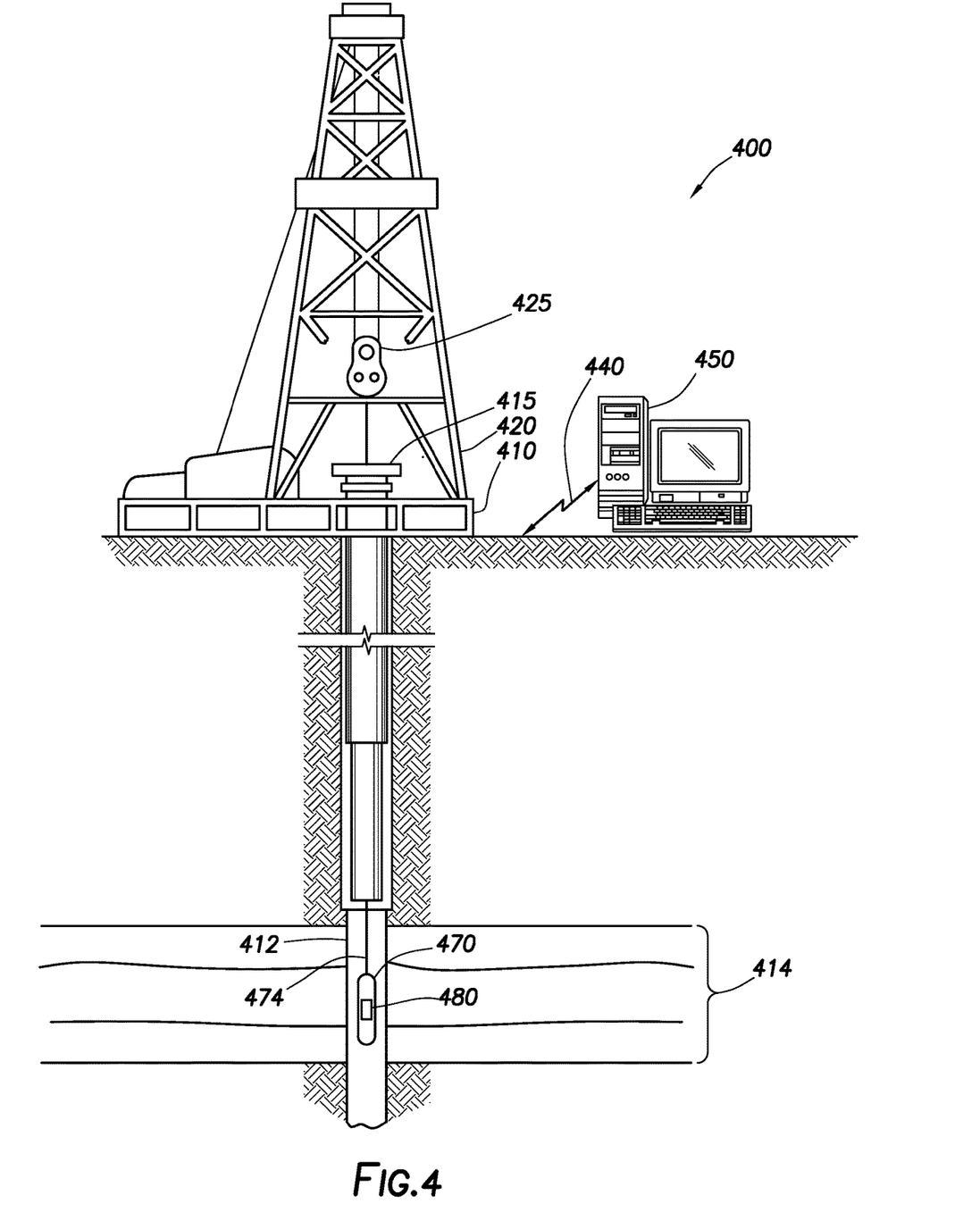
FIG. 4 is a diagram of a system for wireline logging operations in accordance with one or more aspects of the present disclosure.

FIG. 4 shows a system 400 for wireline or slickline logging operations according to certain embodiments of the present disclosure. A drilling platform 410 is equipped with a derrick 420 that supports a hoist 425.

The drilling of oil and gas wells is commonly carried out using a string of drill pipes connected together so as to form a drilling string that is lowered through a rotary table 415 into a wellbore or borehole 412. Here it is assumed that the drill string has been temporarily removed from the borehole 412 to allow a wireline logging tool body 470 to be lowered by wireline, slickline, or logging cable 474 into the borehole 412. Typically, the tool body 470 is lowered to the bottom of the region of interest and subsequently pulled upward at a substantially constant speed.

During the upward or downward trip, at a series of depths the tool movement can be paused and the tool set to pump fluids into sampling and guard probes included in the tool body 470. Various instruments (e.g., compositional sensors) may be used to perform measurements on the subsurface geological formations 414 (e.g., tar mats) adjacent the borehole 412 and the tool body 470. Positioning of the sampling points throughout the wellbore may be selected at least in part based on data from other tests or measurements taken in the formation, among other reasons, to ensure sufficient profile characterization. The measurement data (e.g., data regarding compositional properties of downhole fluids) may be stored and/or processed down hole (e.g., via subsurface processor(s), logic, and memory) or communicated to an information handling system 450 via communications link 440 (which may include wired and/or wireless connections) for storage, processing, and analysis. The information handling system 450 may be provided with electronic equipment for various types of signal processing. Information handling system 450 also may operate in accordance with software (which may be stored on information storage media) and user input via input devices to process and decode the received signals. The resulting data may be further analyzed and processed by information handling system 450 to generate a display of useful information on a computer monitor or some other form of a display device. Similar formation evaluation data may be gathered and analyzed during drilling operations (e.g., during logging while drilling (LWD) operations, and by extension, sampling while drilling).

In certain embodiments, the tool body 470 comprises a formation testing tool 480 for obtaining and analyzing a fluid sample from a subterranean formation through a wellbore. The formation testing tool 480 is suspended in the wellbore by a wireline cable 474 that connects the tool to a surface control unit (e.g., comprising an information handling system 450). The formation testing tool may be deployed in the wellbore on wireline, coiled tubing, jointed drill pipe, hard-wired drill pipe, or via any other suitable deployment technique. In certain embodiments, the formation testing tool 480 may comprise equipment and/or sensors similar to those found in the Reservoir Description Tool (RDT), GEOTAP® tools, or GEOTAP® IDS tools available from Halliburton Energy Services, Inc. However, the tool body 470 may comprise any other sensors or equipment suitable for measuring the properties of a fluid in a well, including but not limited to optical sensors, temperatures sensors, thermal sensors, pressure transducers, phase behavior apparatus and sensors, density sensors, NMR sensors, micro-fluidic sensors, mass spectrometry sensors, chromatographic sensors, and the like.

Figure 5:
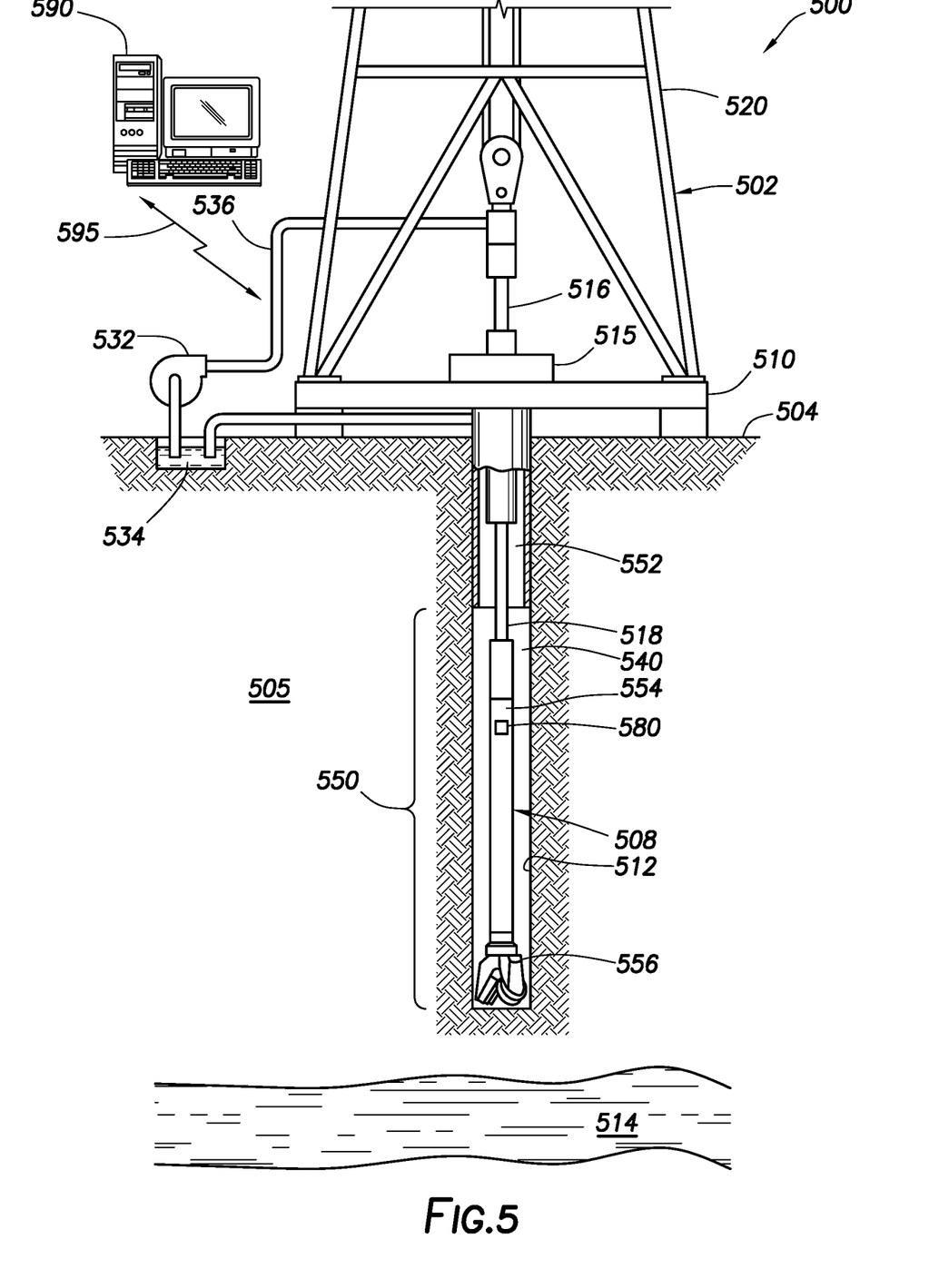
FIG. 5 is a diagram of a system for drilling operations in accordance with one or more aspects of the present disclosure.

FIG. 5 shows a system 500 according to certain embodiments of the present disclosure that may form a portion of a drilling rig 502 located at the surface of a well. Similar to the system shown in FIG. 4, the drilling rig 502 may comprise a platform 510 equipped with a derrick 520 that provides support for a drill string 508. The drill string 508 may operate to penetrate a rotary table 515 for drilling a borehole 512 through a subterranean formation 505, which may include various subsurface formations 514 (e.g., a tar mat). The drill string 508 may include a kelly 516, drill pipe 518, and a bottom hole assembly 550, perhaps located at the lower portion of the drill pipe 518.

The bottom hole assembly 550 may include drill collars 552, a down hole tool 554, and a drill bit 556. The drill bit 556 may operate to create a borehole 512 by penetrating the surface 504 and subsurface formation 514. The down hole tool 554 may comprise any of a number of different types of tools including MWD (measurement while drilling) tools, LWD tools, and others. For example, in certain embodiments, a formation testing tool 580 may be deployed in down hole tool 554 that is used to obtain and analyze a fluid sample from a subterranean formation through a wellbore. The formation testing tool 580 may be connected to a surface control unit (e.g., comprising an information handling system 590) via cables or other devices in the drill string 508. In certain embodiments, the formation testing tool 580 may comprise equipment and/or sensors similar to those found in the Reservoir Description Tool (RDT), GEOTAP® tools, or GEOTAP® IDS tools available from Halliburton Energy Services, Inc. In certain embodiments, drill collars 552 may include logging instruments to gather measurements of various drilling parameters such as position, orientation, weight-on-bit, borehole diameter, etc. The orientation of the down hole tool 554 and/or drill bit 556 may be measured in terms of a tool face angle (rotational orientation), an inclination angle (the slope), and compass direction, each of which can be derived from measurements by magnetometers, inclinometers, and/or accelerometers, though other sensor types such as gyroscopes may alternatively be used.

During drilling operations, the drill string 508 (perhaps including the kelly 516, the drill pipe 518, and the bottom hole assembly 550) may be rotated by the rotary table 515. In addition to, or alternatively, the bottom hole assembly 550 may also be rotated by a motor (e.g., a mud motor) that is located down hole. The drill collars 552 may be used to add weight to the drill bit 556. The drill collars 552 may also operate to stiffen the bottom hole assembly 550, allowing the bottom hole assembly 550 to transfer the added weight to the drill bit 556, and in turn, to assist the drill bit 556 in penetrating the surface 504 and subsurface formation 514. In certain embodiments, the operator can also control the direction of the drill bit 556 along a desired path using any one of various suitable directional drilling systems, including steering vanes, a "bent sub", and a rotary steerable system. In certain embodiments, such systems for controlling the direction of the drill bit 556 may utilize electronic controls that may be controlled, at least in part, by an information handling system or data processor (which, in some embodiments, may comprise the same information handling systems or processors that perform other functions disclosed herein).

Moreover, in some embodiments, a telemetry sub (not shown) coupled to the down hole tools 554 can transmit telemetry data to the surface via any number of known methods, including but not limited to mud pulse telemetry, acoustic telemetry, electromagnetic telemetry, or telemetry via wired drillpipe. Digital signals from the telemetry sub (or from another device that converts the telemetry signals to a digital form) via a communications link 595 to an information handling system 590 such as a computer or other form of a data processing device. Information handling system 590 operates in accordance with software (which may be stored on information storage media) and user input via input devices to process and decode the received signals. The resulting telemetry data may be further analyzed and processed by information handling system 590 to generate a display of useful information on a computer monitor or some other form of a display device. For example, a driller could employ this system to obtain and monitor drilling parameters, formation properties, and the path of the borehole relative to a target location in the formation.

During drilling operations, a mud pump 532 may pump drilling fluid (sometimes known by those of skill in the art as "drilling mud") from a mud pit 534 through a hose 536 into the drill pipe 518 and down to the drill bit 556. The drilling fluid can flow out from the drill bit 556 and be returned to the surface 504 through an annular area 540 between the drill pipe 518 and the sides of the borehole 512. The drilling fluid may then be returned to the mud pit 534, where such fluid is filtered. In some embodiments, the drilling fluid can be used to cool the drill bit 556, as well as to provide lubrication for the drill bit 556 during drilling operations. Additionally, the drilling fluid may be used to remove subsurface formation cuttings created by operating the drill bit 556.

Figure 2:
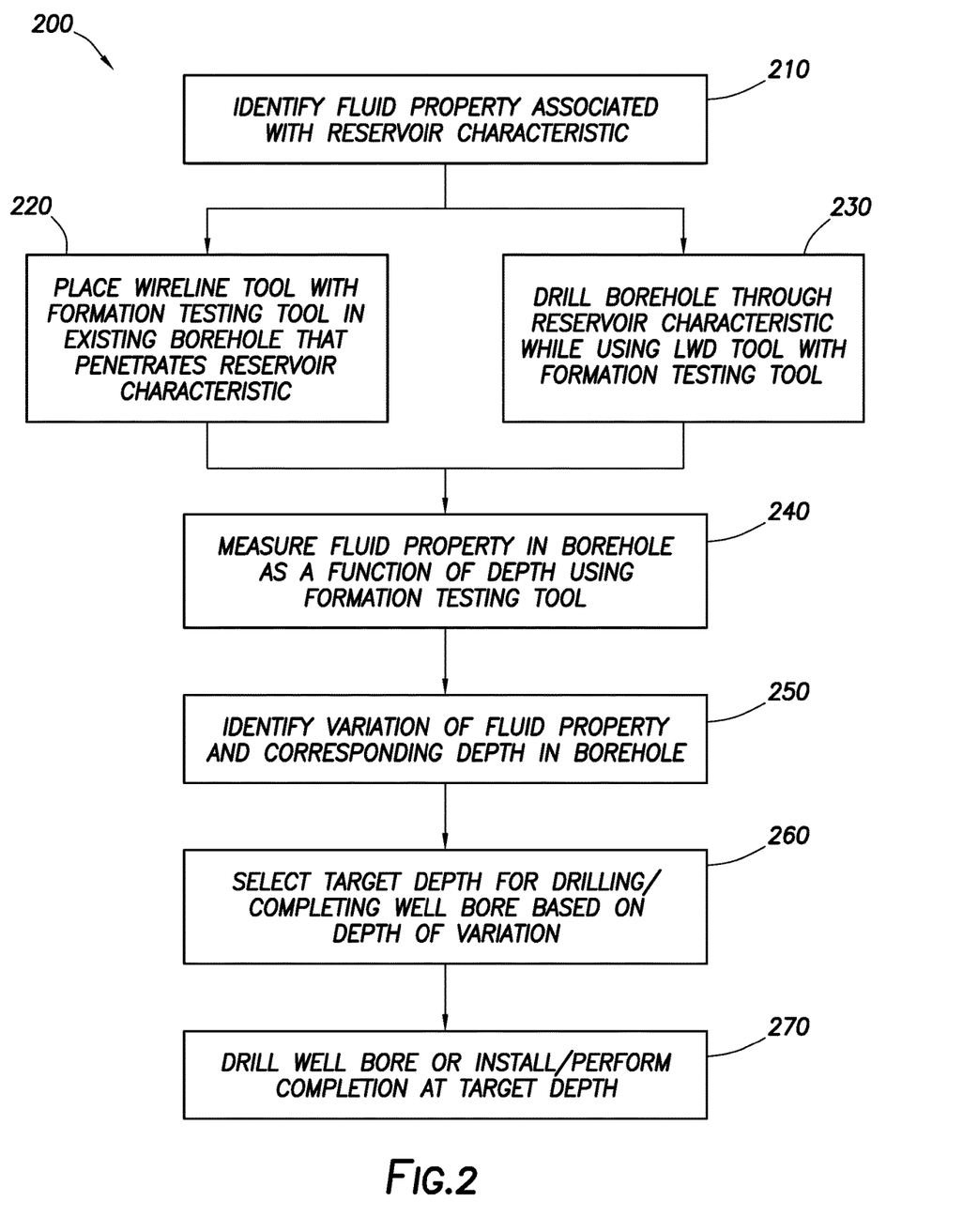
FIG. 2 is a flowchart showing a method of using fluid property logging data to design certain aspects of a well drilling or completions operation in accordance with one or more aspects of the present disclosure.

FIG. 2 is a flowchart illustrating certain methods of the present disclosure 200 in which a target location in a subterranean formation for a portion of a well system is determined based on fluid property data from a borehole penetrating the formation, and then that portion of the well system is drilled or completed in the target location in a separate well bore in that formation. Starting with step 210, a fluid property is identified that is associated with a particular reservoir characteristic of interest (e.g., a tar mat) in the design of the well system. At step 220, a wireline tool comprising a formation testing tool (e.g., tool 470 in FIG. 4) may be placed in an existing borehole that penetrates the formation and the reservoir characteristic itself. Alternatively, at step 230, a borehole may be drilled using a drilling assembly that includes a formation testing tool (e.g., tool 570 in FIG. 5) to penetrate the reservoir characteristic. Whether step 220 or step 330 is used, the process continues to step 240 in which the formation testing tool is used to measure the selected fluid property (e.g., compositional property of a fluid) as a function of depth in the borehole as the wireline tool is raised or lowered in the borehole or as the borehole is drilled. At step 250, the data from the formation testing tool is analyzed to identify a variation in the fluid property and its corresponding location or depth in the borehole. This analysis may comprise, for example, simply inspecting visualizations of the data, or may comprise one or more mathematical analyses of the data (e.g., to find an exact point of inflection and/or variation in the data). Step 250 may be performed in or near real-time with step 240, or may be performed at some time subsequent to step 240. The location or depth identified in step 250 may correspond to the location of a particular reservoir characteristic (or a certain distance therefrom) for which the design of a well system must account. Continuing to step 260, based on the location corresponding to the variation identified in step 250, a target location or depth for a well bore or other component of the well system (e.g., casing, tubing, kickoff point, packer, plug, etc.) is selected. At step 270, a new well bore may be drilled to the target location or depth selected in step 260, or the component of the well system may be installed at that depth or location in a well bore. In certain embodiments, process 200 optionally may comprise an additional step (not shown) at any point prior to step 260 or 270 of confirming the location of the reservoir characteristic using other known methods for detecting the reservoir characteristic in the formation (for example, in the case of tar mats, NMR spectroscopy), among other reasons, to verify and/or calibrate the fluid property measurements.

Figure 3:
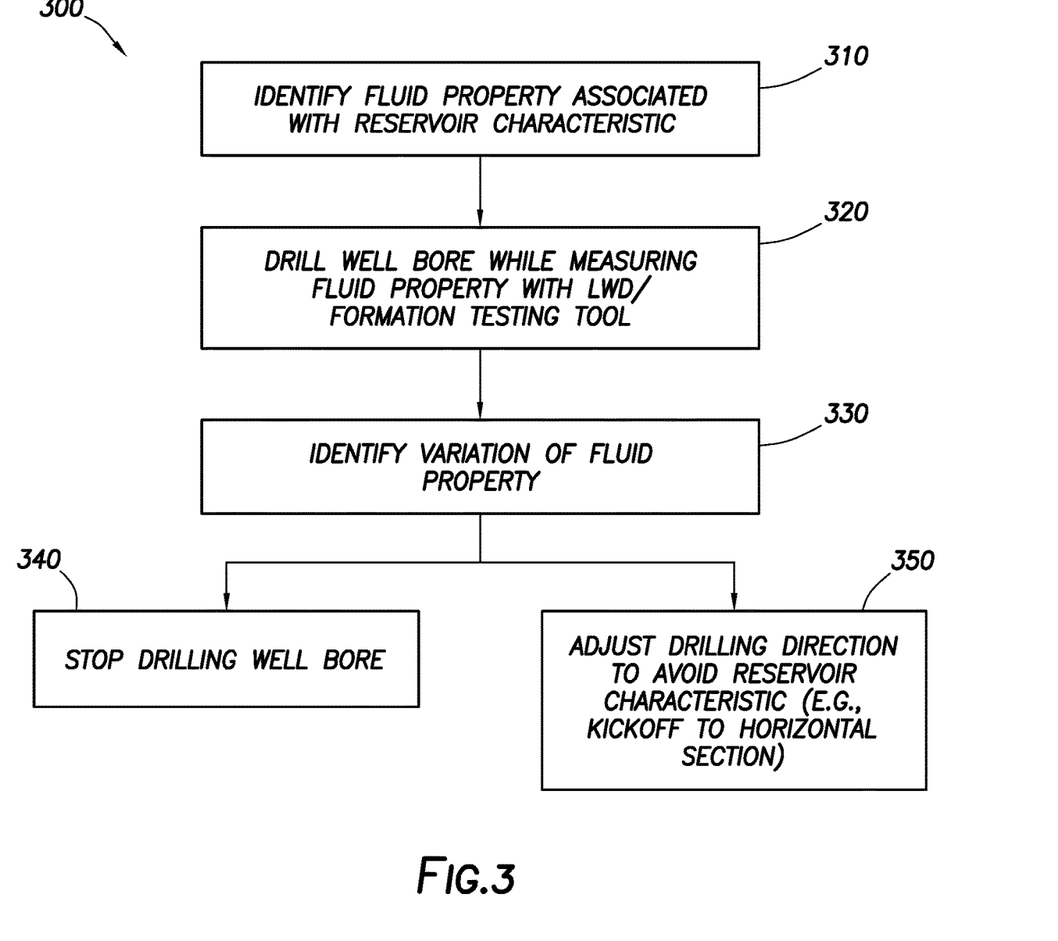
FIG. 3 is a flowchart showing another method of using fluid property logging data to design certain aspects of a well drilling or completions operation in accordance with one or more aspects of the present disclosure.

FIG. 3 is a flowchart illustrating certain methods of the present disclosure 300 in which a portion of borehole is drilled in a subterranean formation for a well system in or to a target location that is determined based on fluid property data from that borehole. In certain embodiments, this may allow an operator to drill a portion of a borehole based on fluid property data without needing to drill a separate borehole or perform wireline operations in order to determine the target location. Starting with step 310, a fluid property is identified that is associated with a particular reservoir characteristic of interest (e.g., a tar mat) in the design of the well system. At step 320, a borehole may be drilled using a drilling assembly that includes a formation testing tool (e.g., tool 570 in FIG. 5) in the formation where the reservoir characteristic of interest resides, and measuring the selected fluid property (e.g., compositional property of a fluid) as a function of depth in the borehole as the borehole is drilled. At step 330, the data from the formation testing tool is analyzed to identify a variation in the fluid property. This analysis may comprise, for example, simply inspecting visualizations of the data, or may comprise one or more mathematical analyses of the data (e.g., to find an exact point of inflection and/or variation in the data). In certain embodiments, step 330 may be performed in or near real-time with step 320, although it generally may be desired to temporarily pause or suspend the rotation and/or advancement of the drill bit in the borehole while the measurements are taken and/or while the data is being analyzed. In these instances, the measurements may be deemed to have been taken "while drilling" the borehole even though the rotation and/or advancement of the drill bit has temporarily stopped. Based on the identification of a variation in the fluid properties, the ongoing drilling of the borehole may be stopped adjusted in or near real-time with that identification. For example, based the variation identified in step 330, it may be determined that the desired bottomhole depth for the borehole has been reached relative to the particular reservoir characteristic, and thus in step 340 drilling operations in that borehole may be stopped. Alternatively, based the variation identified in step 330, it may be determined that the direction of the borehole must be altered, among other reasons, to avoid penetrating the particular reservoir characteristic, and thus in step 350, the direction in which the borehole is drilled may be steered or adjusted (e.g., using the directional drilling equipment shown and described with regard to FIGS. 5 and 6) to a different direction (e.g., a horizontal direction or other non-vertical direction).

Figure 6:
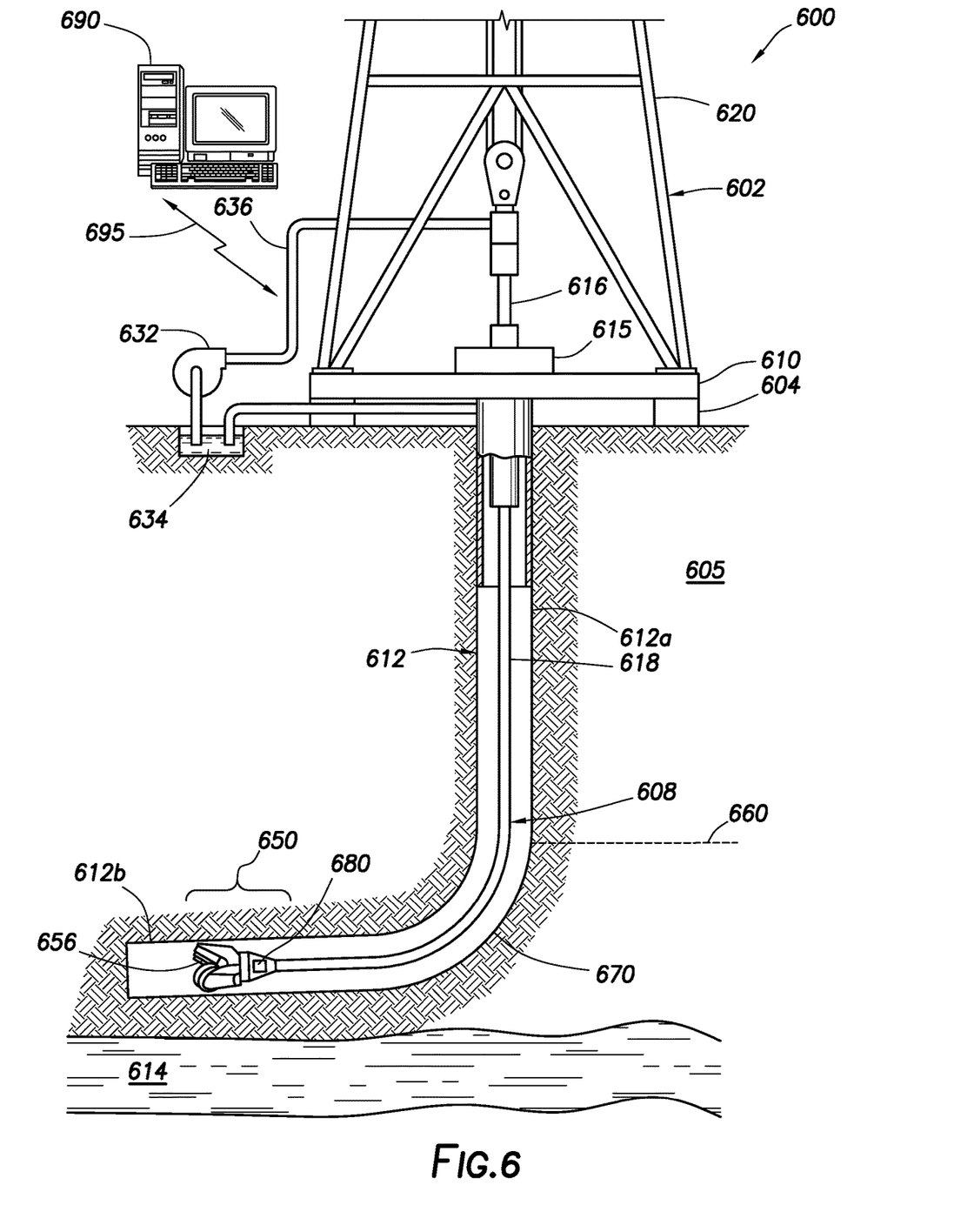
FIG. 6 is a diagram of a system for drilling operations being used to drill a horizontal portion of a borehole in accordance with one or more aspects of the present disclosure.

Turning now to FIG. 6, a directional drilling system 600 similar to that of FIG. 5 is shown in use drilling both a vertical section and a horizontal section of a borehole based at least in part on fluid property data according to certain embodiments of the present disclosure. Like the drilling system of FIG. 5, system 600 includes a drilling rig 602 comprising a platform 610 equipped with a derrick 620 that provides support for a drill string 608 that penetrates a rotary table 615. The drill string 608 includes a kelly 616, drill pipe or coiled tubing 618, and a bottomhole assembly 650, perhaps located at the lower portion of the drill pipe or coiled tubing 618. A formation testing tool 680 may be deployed in bottomhole assembly 650 that is used to obtain and analyze a fluid sample from a subterranean formation through a wellbore. The formation testing tool 680 may be connected to a surface control unit (e.g., comprising an information handling system 690) via cables or other devices in the drill string 608 and/or via a communications link 695 (which may include wired and/or wireless connections). In certain embodiments, the formation testing tool 680 may comprise equipment and/or sensors similar to those found in the Reservoir Description Tool (RDT) and GEO-TAP® tools available from Halliburton Energy Services, Inc. The system 600 may also include a mud pump 632 that pumps drilling mud from a mud pit 634 through a hose 636 and into the drill pipe or coiled tubing 618. In some embodiments, the bottomhole assembly 650 may include a downhole motor (not shown) and a drill bit 656 that is driven by the downhole motor and/or rotation of the drill string 608 to drill a borehole 612 to penetrate the surface 604 and into the formation 605.

The vertical section 612*a* of the borehole 612 may be drilled to a target location or depth 660 identified based on a wireline measurement or previous drilling operation that corresponds to a point just above the tar mat 614. Alternatively, the vertical section 612*a* of the borehole 612 may be drilled to a target location just above the tar mat 614 identified during the drilling operation itself based on fluid property data obtained from formation testing tool 680 during that same drilling operation. When the vertical section 612*a* of the well bore approaches the tar mat 614 (e.g., when the target location 660 is reached, or when a variation in the compositional properties of the fluid in the well bore is detected using formation testing tool 680), the direction of the well may be deflected in a horizontal direction at a kickoff point 670, after which the horizontal section 612*b* of the borehole 612 may be drilled substantially horizontally and thus maintained just above the tar mat 614.

An embodiment of the present disclosure is a method comprising: identifying a reservoir characteristic associated with a chemical or physicochemical property of a fluid in or proximate to the reservoir characteristic; measuring the property of a fluid in at least a portion of a subterranean formation in two or more locations in the subterranean formation; identifying a variation of the property of the fluid at one or more of the locations in the subterranean formation; and determining a target location or direction for a portion of a well system based at least in part on the variation of the property of the fluid, the well system comprising a borehole penetrating the subterranean formation. Optionally, the property of the fluid comprises a concentration of one or more chemical species in the fluid (e.g., one or more aromatic compounds; one or more saturated compounds; one or more residual compounds; and any combination thereof). Optionally, the property comprises at least one property selected from the group consisting of: pH of the fluid; density of the fluid; optical density of the fluid; a nuclear magnetic resonance (NMR) property of the fluid; viscosity of the fluid; viscoelasticity of the fluid; compressibility of the fluid; thermal conductivity of the fluid; heat capacity of the fluid; mass diffusion of the fluid; and any combination thereof. Optionally, the reservoir characteristic comprises a tar mat in the subterranean formation. Optionally, the borehole comprises an injection well penetrating the subterranean formation, and the method further comprises the steps of: drilling the injection well in the subterranean formation in the target location or direction; and injecting one or more fluids into the injection well. Optionally, the measuring step comprises measuring the property of a fluid at two or more depths in a first borehole that penetrates the reservoir characteristic in the subterranean formation; the step of identifying a variation of the property of the fluid comprises identifying the variation of the property of the fluid at a depth in the first borehole; and the portion of the well system is located in a second borehole that penetrates or will penetrate at least a portion of the subterranean formation. Optionally, the method further comprises drilling at least a portion of the borehole in the subterranean formation while measuring the property of the fluid in two or more locations in the borehole; and the determining step further comprises adjusting a direction in which the borehole is drilled based at least in part on the variation of the property of the fluid. Optionally, the method further comprises verifying the location of the reservoir characteristic in the subterranean formation using data other than data relating to the property of the fluid. Optionally, the two or more locations at which the property of the fluid is measured are selected based at least in part on data from tests or measurements taken in the subterranean formation other than the measurement of the property of the fluid. In some embodiments, the methods of the present disclosure may include combinations of any two or more of any of the aforementioned optional features.

Another embodiment of the present disclosure is a system comprising: at least one processor; and a memory coupled to the processor having instructions stored therein, which when executed by the processor, cause the processor to perform functions, including functions to: identify a reservoir characteristic associated with a chemical or physicochemical property of a fluid in or proximate to the reservoir characteristic; measure the property of a fluid in at least a portion of a subterranean formation in two or more locations in the subterranean formation; identify a variation of the property of the fluid at one or more of the locations in the subterranean formation; and determine a target location or direction for a portion of a well system based at least in part on the variation of the property of the fluid, the well system comprising a well bore penetrating the subterranean formation. Optionally, the system further comprises: a bottomhole assembly that comprises at least a downhole tool and a drill bit; and a formation testing tool disposed on the downhole tool and communicatively coupled to the at least one processor. In certain of those embodiments, the instructions in the memory coupled to the processor, when executed by the processor, further cause the processor to control the direction of the drill bit while drilling in the subterranean formation. Optionally, the system further comprises: a wireline logging tool; and a formation testing tool disposed on the wireline logging tool and communicatively coupled to the at least one processor. Optionally, the property of the fluid comprises a concentration of one or more chemical species selected from the group consisting of: one or more aromatic compounds; one or more saturated compounds; one or more residual compounds; and any combination thereof. Optionally, the property comprises at least one property selected from the group consisting of: pH of the fluid; density of the fluid; optical density of the fluid; a nuclear magnetic resonance (NMR) property of the fluid; viscosity of the fluid; viscoelasticity of the fluid; compressibility of the fluid; thermal conductivity of the fluid; heat capacity of the fluid; mass diffusion of the fluid; and any combination thereof. In some embodiments, the systems of the present disclosure may include combinations of any two or more of any of the aforementioned optional features.

Another embodiment of the present disclosure is a computer program product for determining the location of a well system in a subterranean formation, the computer program product comprising a computer readable storage medium readable by a processing device and storing instructions for execution by the processing device for performing the following method: identifying a reservoir characteristic associated with a chemical or physicochemical property of a fluid in or proximate to the reservoir characteristic; measuring the property of a fluid in at least a portion of a subterranean formation in two or more locations in the subterranean formation; identifying a variation of the property of the fluid at one or more of the locations in the subterranean formation; and determining a target location or direction for a portion of a well system based at least in part on the variation of the property of the fluid, the well system comprising a well bore penetrating the subterranean formation. Optionally, the property of the fluid comprises a concentration of one or more chemical species selected from the group consisting of: one or more aromatic compounds; one or more saturated compounds; one or more residual compounds; and any combination thereof.

Although the present disclosure and its advantages have been described in detail, it should be understood that various changes, substitutions and alterations can be made herein without departing from the spirit and scope of the disclosure as defined by the following claims.

What is claimed is:

1. A method, comprising:
   identifying a reservoir characteristic associated with a chemical or physicochemical property of a fluid in or proximate to the reservoir characteristic;
   measuring the property of the fluid in at least a portion of a subterranean formation in two or more locations in the subterranean formation;
   identifying a variation of the property of the fluid at one or more of the locations in the subterranean formation;
   identifying a location of the reservoir characteristic in the subterranean formation based on the variation in the property of the fluid, wherein:
   the property of the fluid is measured above the location of the reservoir characteristic; and
   the location of the reservoir characteristic is identified based on the variation in the property of the fluid above the location of the reservoir; and
   determining a target location or direction for a portion of a well system based at least in part on the location of the reservoir characteristic, the well system comprising a borehole penetrating the subterranean formation.

2. The method of claim 1 wherein the property of the fluid comprises a concentration of one or more chemical species in the fluid.

3. The method of claim 2 wherein the one or more chemical species are selected from the group consisting of: one or more aromatic compounds; one or more saturated compounds; one or more residual compounds; and any combination thereof.

4. The method of claim 1 wherein the property comprises at least one property selected from the group consisting of: pH of the fluid; density of the fluid; optical density of the fluid; a nuclear magnetic resonance (NMR) property of the fluid; viscosity of the fluid; viscoelasticity of the fluid; compressibility of the fluid; thermal conductivity of the fluid; heat capacity of the fluid; mass diffusion of the fluid; and any combination thereof.

5. The method of claim 1 wherein the reservoir characteristic comprises a tar mat in the subterranean formation.

6. The method of claim 1 wherein the borehole comprises an injection well penetrating the subterranean formation.

7. The method of claim 6 further comprising:
   drilling the injection well in the subterranean formation in the target location or direction; and
   injecting one or more fluids into the injection well.

8. The method of claim 1 wherein:
   the measuring step comprises measuring the property of a fluid at two or more depths in a first borehole that penetrates the reservoir characteristic in the subterranean formation;
   the step of identifying a variation of the property of the fluid comprises identifying the variation of the property of the fluid at a depth in the first borehole; and
   the portion of the well system is located in a second borehole that penetrates or will penetrate at least a portion of the subterranean formation.

9. The method of claim 1 wherein:
   the method further comprises drilling at least a portion of the borehole in the subterranean formation while measuring the property of the fluid in two or more locations in the borehole; and
   the determining step further comprises adjusting a direction in which the borehole is drilled based at least in part on the variation of the property of the fluid.

10. The method of claim 9 wherein the borehole comprises an injection well penetrating the subterranean formation.

11. The method of claim 1 further comprising verifying the location of the reservoir characteristic in the subterranean formation using data other than data relating to the property of the fluid.

12. The method of claim 1 wherein the two or more locations at which the property of the fluid is measured are selected based at least in part on data from tests or measurements taken in the subterranean formation other than the measurement of the property of the fluid.

13. A system, comprising:
at least one processor; and
a memory coupled to the processor having instructions stored therein, which when executed by the processor, cause the processor to perform functions, including functions to:
 identify a reservoir characteristic associated with a chemical or physicochemical property of a fluid in or proximate to the reservoir characteristic;
 measure the property of the fluid in at least a portion of a subterranean formation in two or more locations in the subterranean formation;
 identify a variation of the property of the fluid at one or more of the locations in the subterranean formation;
 identifying a location of the reservoir characteristic in the subterranean formation based on the variation in the property of the fluid, wherein:
  the property of the fluid is measured above the location of the reservoir characteristic; and
  the location of the reservoir characteristic is identified based on the variation in the property of the fluid above the location of the reservoir; and
 determine a target location or direction for a portion of a well system based at least in part on the location of the reservoir characteristic, the well system comprising a well bore penetrating the subterranean formation.

14. The system of claim 13 further comprising:
 a bottomhole assembly that comprises at least a downhole tool and a drill bit; and
 a formation testing tool disposed on the downhole tool and communicatively coupled to the at least one processor.

15. The system of claim 14 wherein the instructions in the memory coupled to the processor, when executed by the processor, further cause the processor to control the direction of the drill bit while drilling in the subterranean formation.

16. The system of claim 13 further comprising:
 a wireline logging tool; and
 a formation testing tool disposed on the wireline logging tool and communicatively coupled to the at least one processor.

17. The system of claim 13 wherein the property of the fluid comprises a concentration of one or more chemical species selected from the group consisting of: one or more aromatic compounds; one or more saturated compounds; one or more residual compounds; and any combination thereof.

18. The system of claim 13 wherein the property comprises at least one property selected from the group consisting of: pH of the fluid; density of the fluid; optical density of the fluid; a nuclear magnetic resonance (NMR) property of the fluid; viscosity of the fluid; viscoelasticity of the fluid; compressibility of the fluid; thermal conductivity of the fluid; heat capacity of the fluid; mass diffusion of the fluid; and any combination thereof.

19. A computer program product for determining the location of a well system in a subterranean formation, the computer program product comprising a computer readable storage medium readable by a processing device and storing instructions for execution by the processing device for performing the following method:
 identifying a reservoir characteristic associated with a chemical or physicochemical property of a fluid in or proximate to the reservoir characteristic;
 measuring the property of fluid in at least a portion of a subterranean formation in two or more locations in the subterranean formation;
 identifying a variation of the property of the fluid at one or more of the locations in the subterranean formation;
 identifying a location of the reservoir characteristic in the subterranean formation based on the variation in the property of the fluid, wherein:
  the property of the fluid is measured above the location of the reservoir characteristic; and
  the location of the reservoir characteristic is identified based on the variation in the property of the fluid above the location of the reservoir; and
 determining a target location or direction for a portion of a well system based at least in part on the location of the reservoir characteristic, the well system comprising a well bore penetrating the subterranean formation.

20. The computer program product of claim 19 wherein the property of the fluid comprises a concentration of one or more chemical species selected from the group consisting of: one or more aromatic compounds; one or more saturated compounds; one or more residual compounds; and any combination thereof.

* * * * *